United States Patent [19]

Le Thiesse et al.

[11] Patent Number: 5,766,521
[45] Date of Patent: Jun. 16, 1998

[54] PROCESS FOR OBTAINING CRISTALLIZED PEARLS EXHIBITING THE PHENOMENON OF SUPERCOOLING

[75] Inventors: Jean-Claude Le Thiesse, Saint-Etienne; Eraclis Statiotis, Villette D'Anthon, both of France

[73] Assignee: Rhone-Poulenc Chimie, Courbevoie, France

[21] Appl. No.: 629,859

[22] Filed: Apr. 9, 1996

[30] Foreign Application Priority Data

Apr. 10, 1995 [FR] France ................ 95 04260

[51] Int. Cl.$^6$ .................. B29B 9/10; B29C 35/02
[52] U.S. Cl. .................. 264/7; 264/14
[58] Field of Search .................. 264/7, 13, 14, 264/5, 345

[56] References Cited

U.S. PATENT DOCUMENTS

| | | | |
|---|---|---|---|
| 3,450,804 | 6/1969 | Boecknio | 264/14 |
| 4,086,346 | 4/1978 | Bocker et al. | 264/13 |
| 4,340,550 | 7/1982 | Ho | 264/13 |
| 4,390,483 | 6/1983 | Willems et al. | |
| 5,040,960 | 8/1991 | Shioya et al. | 264/14 |
| 5,188,838 | 2/1993 | Deleuil et al. | |
| 5,290,913 | 3/1994 | McAllister et al. | 264/9 |
| 5,310,792 | 5/1994 | Inoue | 525/64 |
| 5,360,616 | 11/1994 | Garza Flores et al. | |
| 5,380,532 | 1/1995 | Deleuil et al. | |
| 5,540,868 | 7/1996 | Stouffer et al. | 264/13 |

FOREIGN PATENT DOCUMENTS

| | | |
|---|---|---|
| 95-091129 | 12/1994 | Brazil. |
| 0 438 359 | 7/1991 | European Pat. Off.. |
| 81/02890 | 10/1981 | WIPO. |
| 91/19484 | 12/1991 | WIPO. |

OTHER PUBLICATIONS

Organic Polymers, Alfrey and Gurnee, pp. 12–14, ©1967.

*Primary Examiner*—David A. Simmons
*Assistant Examiner*—Kenneth M. Jones
*Attorney, Agent, or Firm*—Katherine L. Carleton; John Daniel Wood; Jean-Louis Seugnet

[57] ABSTRACT

The present invention relates to a novel presentation of a product exhibiting the phenomenon of supercooling. More precisely, the subject of the invention is cristallized pearls of a product exhibiting strong supercooling. The invention also relates to the preparation of the said pearls. The characteristic feature of the process of the invention is to melt, if necessary, the product to be shaped; to break up the molten mass into droplets; to cool the droplets to a temperature below the glass transition temperature of the product, so that these droplets harden by vitrification; to maintain the pearls thus vitrified at a temperature below the glass transition temperature and to place them in contact with crystallization seeds; to crystallize the pearls by raising the temperature above the glass transition temperature and then to recover the crystallized pearls.

31 Claims, 4 Drawing Sheets

PROCESS FOR OBTAINING CRISTALLIZED PEARLS EXHIBITING THE PHENOMENON OF SUPERCOOLING

BACKGROUND OF THE INVENTION

The present invention relates to a novel presentation of a product exhibiting the phenomenon of supercooling. More precisely, the subject of the invention is cristallized pearls of a product exhibiting strong supercooling. The invention also relates to a process for the preparation of the said pearls.

In many fields of application, it is required that the products used are in a form which must satisfy many requirements:

the product must be easy to handle, the particle size distribution of the product must exclude fine particles which generate dusts, particles of less than about 100 μm, the product must exhibit good flow properties and must not cake in temporary storage installations, of the hopper type, or during use in processes of subsequent transformation, or during prolonged storage in the usual packaging.

These requirements may be more or less fully satisfied by making the product available in the form of a powder of coarse particle size.

It may be envisaged to obtain such a particle size by an operation of solution crystallization. However, such a technique has its limits since it is not always easy to control the crystal growth and, in the case of anisotropy, the crystals obtained are fragile and do not meet the demands as regards mechanical properties.

It is also possible to make use of powder shaping techniques such as granulation but, in general, these techniques require the use of an additive as binder. It is also possible to carry out the "prilling" technique, which consists in melting the product and in breaking it up into droplets which are solidified by cooling.

The problem which then arises is that many products, in particular starting materials in the pharmaceutical or agrochemical field, exhibit a phenomenon of supercooling, that is to say that when the product is melted and is cooled below its melting point, it does not crystallize and remains in the liquid state. It follows therefrom that when a product exhibits the phenomenon of supercooling, and this is especially the case for glyceryl guaiacolate, real difficulties exist in carrying out a prilling technique.

SUMMARY OF THE INVENTION

The subject of the present invention is, precisely, the provision of a process which makes it possible to shape a product which exhibits supercooling.

Another subject of the invention is that it leads to a product which satisfies all the abovementioned requirements.

Lastly, another subject is a novel form or presentation of a product exhibiting a phenomenon of supercooling, without a crystallization additive being included therein.

The subject of the present invention is cristallized pearls of a product exhibiting supercooling so that a glass transition is revealed and comprising no crystallization additives.

In the account of the present invention, the term "pearls" refers to solid particles of high sphericity.

The characteristic feature of the process of the invention, for the purpose of preparing cristallized pearls of a product exhibiting the phenomenon of supercooling, consists:

in melting, if necessary, the said product, in breaking up the molten mass into droplets, in cooling the droplets to a temperature below the glass transition temperature of the product, so that these droplets harden by vitrification, in maintaining the pearls thus vitrified at a temperature below the glass transition temperature and in placing them in contact with crystallization seeds, in crystallizing the pearls by gradually raising the temperature above the glass transition temperature, in recovering the crystallized pearls.

A preferred variant of the process of the invention consists in melting, if necessary, the product to be shaped and then in passing the molten mass through a nozzle so as to form droplets, in solidifying these droplets by allowing them to fall in a tower with a countercurrent of a cold gas, and then in recovering the vitrified pearls which are subsequently converted into crystallized pearls according to the steps described above.

DESCRIPTION OF THE PREFERRED EMBODIMENT(s)

The process of the invention is entirely suitable for the preparation of pearls of a product exhibiting strong supercooling.

It will be recalled that the term "supercooling" defines the state of a body which remains liquid below its melting point.

The process of the invention is entirely suitable for shaping, in particular, organic products used in the pharmaceutical and agrochemical fields.

Specific examples which may be mentioned are glyceryl guaiacolate, propionic acid derivatives and more particularly 2-(3-benzoylphenyl)propionic acid (Ketoprofen®), 2-(4-isobutylphenyl)propionic acid (Ibuprofen®) and 2-methyl-3propyl-1,3-propanediol dicarbonate or meprobamate.

The pearls obtained according to the invention have physicochemical characteristics which are intrinsic to them.

The pearls obtained have a size of particles essentially in spherical form, having a diameter which may be chosen, by means of the process of the invention, from within a wide range. Thus, the particle size expressed by the median diameter (d50) may range between 100 μm and 3,000 μm but is preferably between 500 μm and 2,000 m.

The median diameter is defined as being such that 50% by weight of the particles have a diameter above or below the median diameter.

It should be pointed out that the sizes are determined by passage through metal sieves.

Depending on the starting material and its field of application, the chosen particle size may be more or less coarse. Thus, in the case of glyceryl guaiacolate which constitutes a preferred application of the process of the invention, the median diameter is preferably between 500 μm and 1,000 μm.

Figure 1:
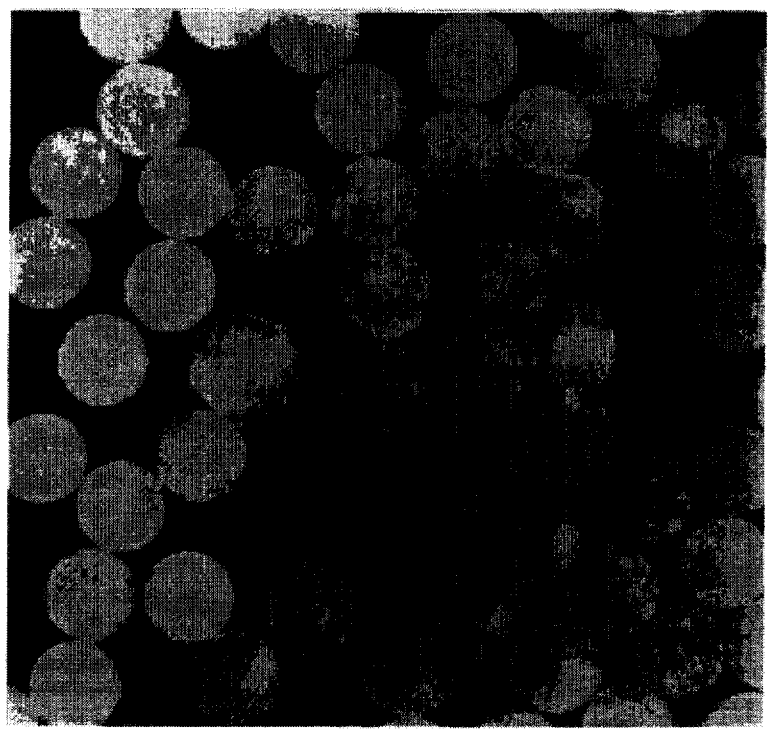
FIG. 1 is a photograph taken an an optical microscope of pearls of glyceryl guaiacolate as produced in Example 1.

FIG. 1 represents a photograph taken on an optical microscope (G=18) which shows the morphology of spherule type of a product exhibiting strong supercooling such as glyceryl guaiacolate.

Uniform particle size distribution is observed for the product obtained.

Figure 2:
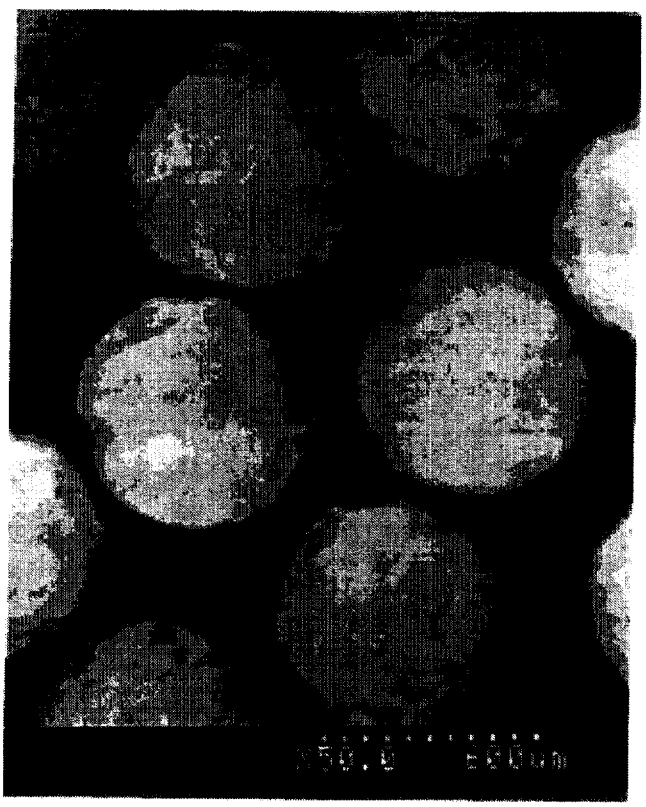
FIG. 2 is a photograph taken on a scanning electron microscope of pearls of glyceryl guaiacolate as produced in Example 1.

FIG. 2 represents a photograph taken on a scanning electron microscope (G=50) which reveals the surface aspect of the pearls obtained.

The novel structure of the products of the invention is obtained by means of an entirely adapted manufacturing process.

The process of the invention for the preparation of cristallized pearls of a product exhibiting the phenomenon of supercooling thus consists:

in melting, if necessary, the said product, in breaking up the molten mass into droplets, in cooling the droplets to a temperature below the glass transition temperature of the product, so that these droplets harden by vitrification, in maintaining the pearls thus vitrified at a temperature below the glass transition temperature and in placing them in contact with crystallization seeds, in crystallizing the pearls by gradually raising the temperature above the glass transition temperature, in recovering the crystallized pearls.

In the process of the invention, a product in the molten state is used.

It may be envisaged to supply the molten product originating from a manufacturing line directly. This is particularly advantageous when the starting material is a heat-sensitive product.

If a pulverulent solid form is available, it is necessary to provide an invention process step which consists in melting the said product. To this end, the product is heated to its melting point. Preferably, the product is taken to a temperature slightly above its melting point, preferably not more than 5° C. above its melting point. For glyceryl guaiacolate specifically, the temperature to which it is taken is chosen between 83° C. and 88° C.

This operation is generally carried out with stirring.

The molten mass is converted into droplets in a following step. This operation may be performed using a fragmentation device of any type, for example a round-holed flat nozzle.

A preferred embodiment of the invention consists in forming the droplets by passing the molten mass through an orifice and most particularly by passage through a nozzle.

The following operation is to ensure the hardening of the droplets into vitrified pearls by contact with a cold fluid whose temperature is chosen such that it is less than the glass transition temperature of the product to be shaped.

The expression "glass transition temperature" means the temperature at which a material passes from the glassy state to the non-rigid solid state.

The glass transition temperature is determined in a known manner and more particularly according to AFNOR standard T51-507-2 of Dec. 1991.

The temperature of the cold fluid is preferably 10° to 20° C. lower than the glass transition temperature. In the case of glyceryl guaiacolate, the temperature of the cold fluid is chosen between −60° C. and −30° C., preferably between −60° C. and −40° C.

In general, the lower limit is not critical in any way. It is only limited by technological and/or economic considerations.

The cold fluid is more particularly a cold gas and preferably air, but the invention does not exclude any particular gas, provided that it is inert towards the product to be shaped. Nitrogen may be chosen but, in general, air or oxygen-depleted air (for example depleted to a concentration of 10%) is preferred in the case where the product is oxidizable or inflammable.

The cold gas stream is preferably sent in in countercurrent to the flow of material.

The residence time, which is the duration between the formation of the droplet to the emergence from the nozzle and its arrival into the recovery system, is advantageously between 1 and 10 seconds and more preferably between 1 and 3 seconds.

One way of obtaining the desired residence time is to let the droplets fall in a tower with a countercurrent of a cold gas as mentioned above.

At the end of the reaction, the vitrified pearls are recovered by any known means, for example by gravity in a recovery vat or, preferably, according to the fluid bed technique.

The vitrified pearls are converted into crystallized pearls in a following step.

To this end, the vitrified pearls are maintained at a temperature below the glass transition temperature, preferably 5° to 10° C. below the glass transition temperature, and they are placed in contact with crystallization seeds.

For glyceryl guaiacolate pearls, the temperature is advantageously chosen between −30° C. and −35° C.

The crystallization seeds consist of a small amount of crystalline powder of the same nature as the product to be shaped.

The size of the particles in the powder is much smaller than that of the obtained pearls, preferably their diameter is below the value corresponding to 1/10 of the diameter of the pearls obtained.

It is chosen to use seeds in an amount representing, for example, from 0.1 to 5% relative to the weight of the vitrified pearls.

In order to trigger the crystallization, the temperature is gradually raised to a temperature at least equal to the glass transition temperature and up to the temperature which corresponds to the exothermy associated with crystallization of the pearls.

The upper temperature limit is preferably 10° to 20° C. above the glass transition temperature.

The temperature increase is preferably carried out gradually. To this end, the temperature may, for example, be raised by 0.5° to 1° C. per minute.

The duration of this operation varies widely and, as a guide, it is pointed out that a duration of 10 min to 2 hours is generally necessary to convert the vitrified pearls into crystallized pearls.

The crystallized pearls are recovered by any known means, but preferably using a device which allows the heat released by the crystallization to be removed rapidly. Thus, a fluid bed is well suited to carrying out the final step of the process of the invention.

The pearls of a product exhibiting supercooling thus obtained according to the process of the invention have the characteristics described above.

As regards the apparatus used to carry out the process of the invention, this is composed of three assemblies: a first assembly for shaping the pearls, a second assembly for recovery of the vitrified pearls and a third assembly for crystallization of the vitrified pearls.

The first assembly comprises a storage vat which is preferably stirred when the product to be shaped originates from a manufacturing line, or alternatively a melting device which makes it possible to melt the product if it is in pulverulent form, and a chamber which is generally a tower whose height preferably ranges between 4 and 8 metres, comprising, in its upper part, a device for fragmentation into droplets, preferably a nozzle, and equipped in its lower part with one or more cold gas stream inlets, thus transforming the bottom of the tower into a cooling tower.

The product to be shaped is introduced via a twin-screw hopper into a melting device which is a reactor equipped with a system which allows the temperature to be adjusted, for example a jacket, so as to maintain the said product in the molten state.

The nozzle used may be a single-hole nozzle or a multi-hole nozzle with a number of holes which may range between 1 and 100.

A system may be used comprising several nozzles, for example 2 nozzles, which are preferably movable and in parallel.

The diameter of the nozzle perforations is a function of the size of pearls desired. It may be from 50 to 2,000 μm but is preferably chosen between 200 and 600 μm.

The size of the perforation is always less than the size of the spherule obtained. Thus, a nozzle having perforations of about 200 μm is used in order to obtain pearls having a median diameter of 550 μm.

The nozzle used may be a static nozzle but it is possible to make use of a nozzle subjected to a system of high frequency vibration, for example at 100 to 10,000 hertz.

The molten product arrives into the nozzle either using a volumetric pump or via a positive pressure which is provided by a gas stream, preferably a stream of nitrogen. The positive pressure relative to atmospheric pressure is from 5 to 500%.

The nozzle is maintained at a temperature slightly above the melting point of the product, preferably 2° to 5° C. above this temperature.

At the nozzle, it is possible but not essential to establish a gas stream, preferably a co-current of air or of nitrogen, with the jet leaving the nozzle. This gas stream is preferably at a temperature between room temperature and 80° C. The presence of this gas co-current makes it possible to obtain better uniformity of the dimension of the pearls and avoids coalescence of the drops.

In the upper part of the tower there may be chicanes and grilles present on the inner wall, these allowing homogenization of the gas flow.

In the bottom of the tower, a stream of cold gas, preferably a stream of cold air, is introduced in order to ensure hardening of the droplets into vitrified pearls. It is at a temperature chosen such that it is less than the glass transition temperature of the product to be shaped, preferably at a temperature 10° to 20° C. lower than the glass transition temperature.

The cold gas preferably leaves the tower, below the nozzle, at a distance advantageously representing one-tenth of the total height of the cooling zone.

The system of pearl recovery at the bottom of the tower is chosen such that it allows the vitrified pearls to be kept at a temperature below the glass transition temperature of the product. It may consist of a refrigerated recovery vat but it is preferable to make use of a device which makes it possible to ensure fluidization of the bed of particles. It thus consists of a vat, preferably a cylindrical one, containing in its lower part a grille through which is sent a gas stream, preferably nitrogen, air or oxygen-depleted air. The gas flow rate, which depends on the size of the particles, must be such that it keeps the particles in suspension. It is pointed out by way of example that this flow rate is from 5 to $30^3$/h for a fluid bed diameter of 80 mm.

In this part of the apparatus the cooling is necessarily continued, since the temperature of the fluidization gas (preferably air) sent in is at the same temperature (±5° C.) as the temperature of the cold gas stream sent to the bottom of the tower.

An outlet is arranged in the fluidization device, allowing the evacuation of the vitrified pearls.

The third assembly corresponds to a part of the apparatus in which the crystallization is carried out. This operation is performed in a fluid bed device or any other device, for example a vibrating passage, which allows the vitrified pearls to be placed in contact with the crystallization seeds and ensures a gradual rise in temperature.

A first variant consists in carrying out this operation in the same fluidization device used in the preceding step. Thus, once the vitrified pearls have been formed, the fluidization gas is sent in at a temperature below the glass transition temperature of the product, preferably 5° to 10° C. below, and the crystallization seeds are then introduced either via the evacuation outlet or by any means provided for this purpose.

The pearls are crystallized by raising their temperature above the glass transition temperature. The fluidization gas is thus sent in at a suitable temperature and the temperature increase is controlled, which then results from the crystallization, cooling if necessary. The temperature rise is advantageously from 0.5° to 1° C. per minute.

The temperature is increased until the exothermy associated with crystallization of the pearls is noted.

The flow rate of the fluidization gas is advantageously raised so as to remove the heat released. By way of example, it is pointed out that this flow rate is from 80 to 200 $m^3$/h, per kg of pearls, for a fluid bed diameter of 150 mm.

Next, the crystallized pearls are removed using a suitable device.

Another variant of the process of the invention consists in providing a second fluidization device placed after the preceding one.

The vitrified pearls coming from the first fluid bed are mixed with the crystallization seeds and fall into a second fluid bed in which the temperature of the fluidization gas is at least equal to the glass transition temperature, preferably slightly above the said temperature. As mentioned above, care is taken to raise the temperature gradually.

Once the pearls have crystallized, they are removed in a standard manner.

Figure 3:
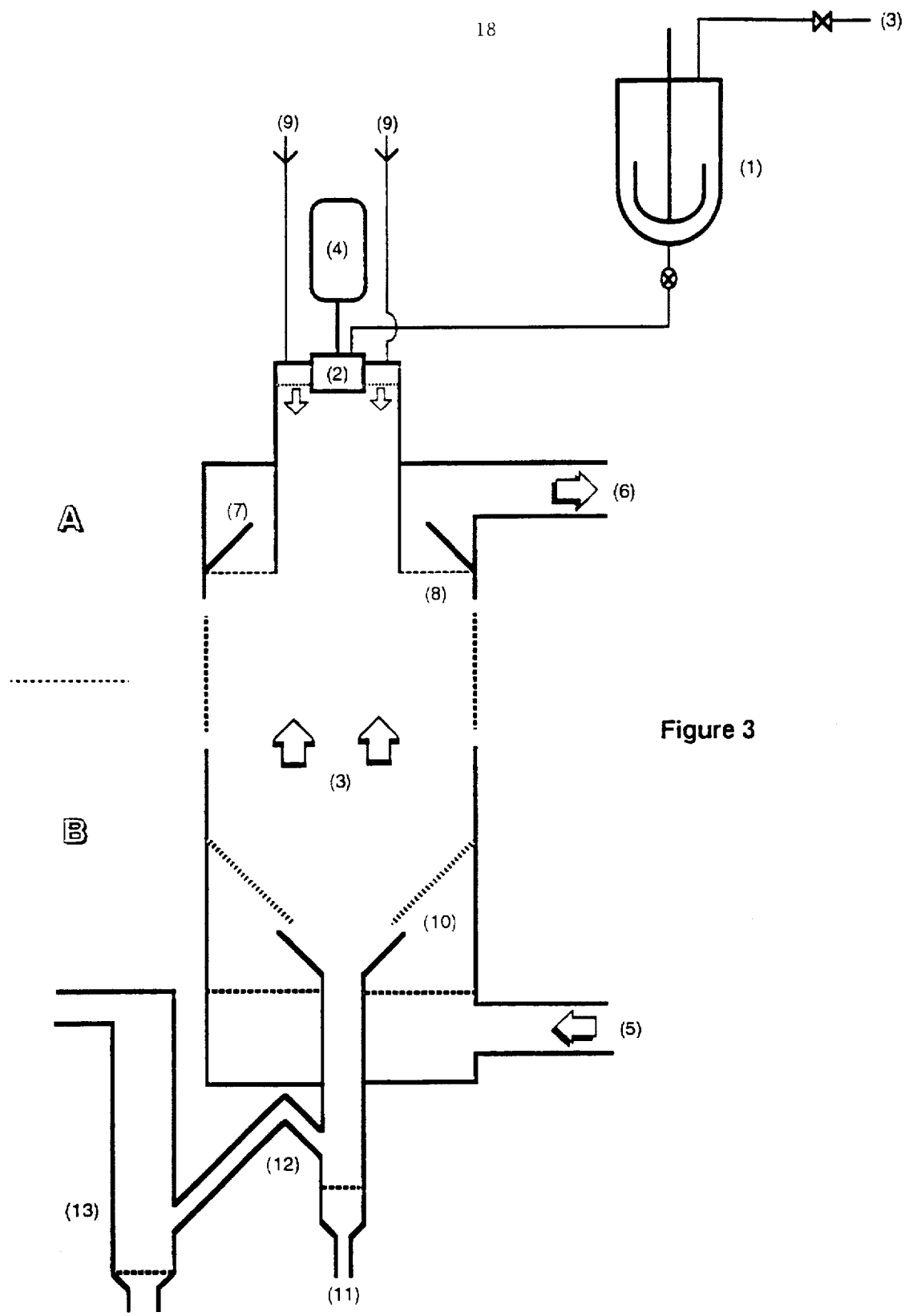
FIG. 3 is a schematic side view of an apparatus for carrying out the vitrification and crystallization process of the invention.

A practical embodiment of the invention is illustrated by the attached drawing in the form of FIG. 3.

FIG. 3 is a schematic side view of an apparatus adapted to carry out the invention.

The apparatus used consists of two parts: the upper part or prilling tower (A) and the lower part which schematizes the fluidization devices (B).

The powder to be shaped is introduced into the pot (1) where it is melted before being conveyed to the nozzle (2). For this, nitrogen (3) is admitted at a positive pressure into the reserve tank (1).

The tower, 8 metres high, comprises in its upper part a nozzle (2) attached to a vibrator (4) and is equipped in its lower part with an inlet of a stream of cold air (5).

The cooling air introduced at (5) leaves the tower at point (6) below the nozzle (2).

In the upper part of the tower, chicanes (7) and a ring-shaped grille (8) ensure homogeneous distribution of the gas flow in the tower.

A flow of hot nitrogen (9) having a temperature of between 20° C. and 80° C., preferably between 60° C. and 80° C., is distributed around the nozzle (2) in co-current.

In the lower part of the tower, a frustoconical grille (10) allows the solidified vitrified pearls to be collected in a fluidization device comprising a nitrogen inlet at (11) and an outlet (12) which serves to transfer the vitrified pearls to a second fluidized bed (13) where the crystallization seeds are introduced and where the crystallization of the pearls is triggered by raising their temperature above the glass transition temperature.

Practical exemplary embodiments of the invention are given below:

EXAMPLES

The operating procedure which will be used in the following Examples 1 and 2 is defined below.

1 kg of a product exhibiting strong supercooling, namely glyceryl guaiacolate, is used.

The process of the invention is carried out in the apparatus described above and represented schematically by FIG. 3.

The nozzle, subjected to vibrations, has characteristics specified in the following examples.

The powder of the product to be shaped is introduced into the pot (1).

The said product is melted in the melting device by heating using hot water circulating in the jacket.

The temperature of the product is 84° C. at (1) for glyceryl guaiacolate. The temperature at (2) at the nozzle outlet and the flow rate of the product are specified below.

Cooling air is introduced at (5) at a flow rate of 850 m³/h, i.e. a speed in the tower of 0.6 m/s. The air leaves at (6).

The air temperatures at the tower inlet (5) and at the tower outlet at (6) are specified in a summarization table given in each example.

This is likewise the case for the temperature of the fluidization air at (11).

Figure 4:
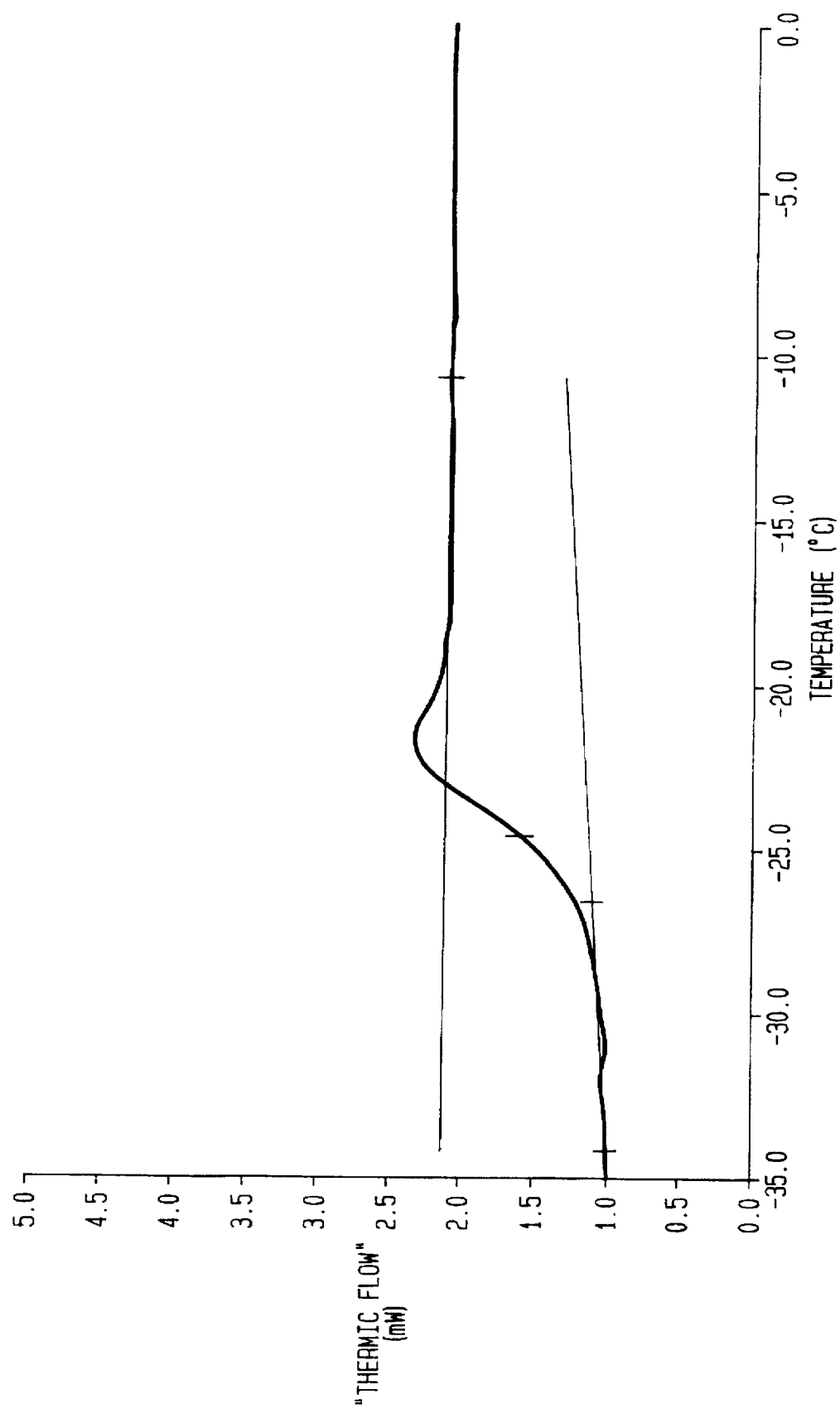
FIG. 4 is a differential thermal analysis curve showing the glass transition temperature of guaiacolate.

The vitrified pearls obtained are collected at (10) and evacuated at (12) towards the fluidized bed (13), where they are kept in fluidization at a temperature of −35° C. until the end of the prilling operation; the glass transition temperature is about −25° C., as revealed in FIG. 4 which is a differential thermal analysis curve obtained for a heating rate of 5° C./min (determined on a Perkin-Elmer® machine), which represents the variation in heat flow (expressed in mW) as a function of the temperature (expressed in °C.).

Finely powdered glyceryl guaiacolate is introduced at (13) in order to form crystallization seeds and the temperature of the fluidization air at (13) is then raised at a rate of 0.5° C./min.

When the temperature reaches 2° to 3° C., an exothermy associated with crystallization of the pearls is recorded.

A fluidization air flow rate of 100 m³/h at (13) allows the heat released to be removed rapidly and prevents the temperature of the product from rising above 20° C.

Example 1

The glyceryl guaiacolate pearls are prepared in an apparatus as represented schematically by FIG. 3, including a 1-hole nozzle. The L/D ratio is 3, L representing the length of the orifice and D its diameter.

The process carried out is as described above: the running conditions are specified in Table I below:

TABLE I

| | |
|---|---|
| Diameter of the nozzle hole | 250 μm |
| Frequency of vibration of the nozzle (2) | 970 Hz |
| Positive pressure of nitrogen (3) | 0.22 bar |
| Temperature of the molten product at (2) | 86° C. |
| Flow rate of the product at the nozzle outlet (2) | 0.410 kg/h |
| Tower inlet (5) air temperature | −60° C. |
| Tower outlet (6) air temperature | −45° C. |
| Fluid bed (11) air temperature | −55° C. |
| Fluid bed (13) air temperature | −35° C. |

After functioning for 120 minutes, 820 g of vitrified pearls are recovered in the fluid bed (13).

10 g of glyceryl guaiacolate powder are added at (13).

The fluid bed (13) air temperature is increased.

The rate of temperature increase is 0.5° C./min.

The final fluidization temperature is +18° C.

After fluidization for 110 minutes, 820 g of crystallized pearls having a diameter of 570 μm are recovered. They are separated from the excess powder which served as crystallization seeds, by simple screening.

Example 2

Glyceryl guaiacolate pearls are prepared as in Example 1: the modifications of the process parameters are specified in the following table:

TABLE II

| | |
|---|---|
| Diameter of the nozzle hole | 400 μm |
| Frequency of vibration of the nozzle (2) | 1010 Hz |
| Positive pressure of nitrogen (3) | 0.17 bar |
| Temperature of the molten product at (2) | 84° C. |
| Flow rate of the product at the nozzle outlet (2) | 0.870 kg/h |
| Tower inlet (5) air temperature | −60° C. |
| Tower outlet (6) air temperature | −45° C. |
| Fluid bed (11) air temperature | −55° C. |
| Fluid bed (13) air temperature | −35° C. |

After functioning for 60 minutes, 870 g of vitrified pearls are recovered in the fluid bed (13).

10 g of glyceryl guaiacolate powder are added at (13).

The fluid bed (13) air temperature is increased.

The rate of temperature increase is 0.5° C./min.

The final fluidization temperature is +18° C.

After fluidization for 110 minutes, 870 g of crystallized pearls having a diameter of 720 μm are recovered. They are separated from the excess powder which served as crystallization seeds, by simple screening.

The product obtained exhibits a morphology in the form of pearls illustrated by FIGS. 1 and 2, which represent photographs taken on an optical microscope (G=18) and on a scanning electron microscope (G=50).

Example 3

In this example, pearls of 2-(3-benzoylphenyl)propionic acid (Ketoprofen®) are prepared in an apparatus as represented schematically by FIG. 3, including a 1-hole nozzle with an L/D ratio of 3.

Figure 5:
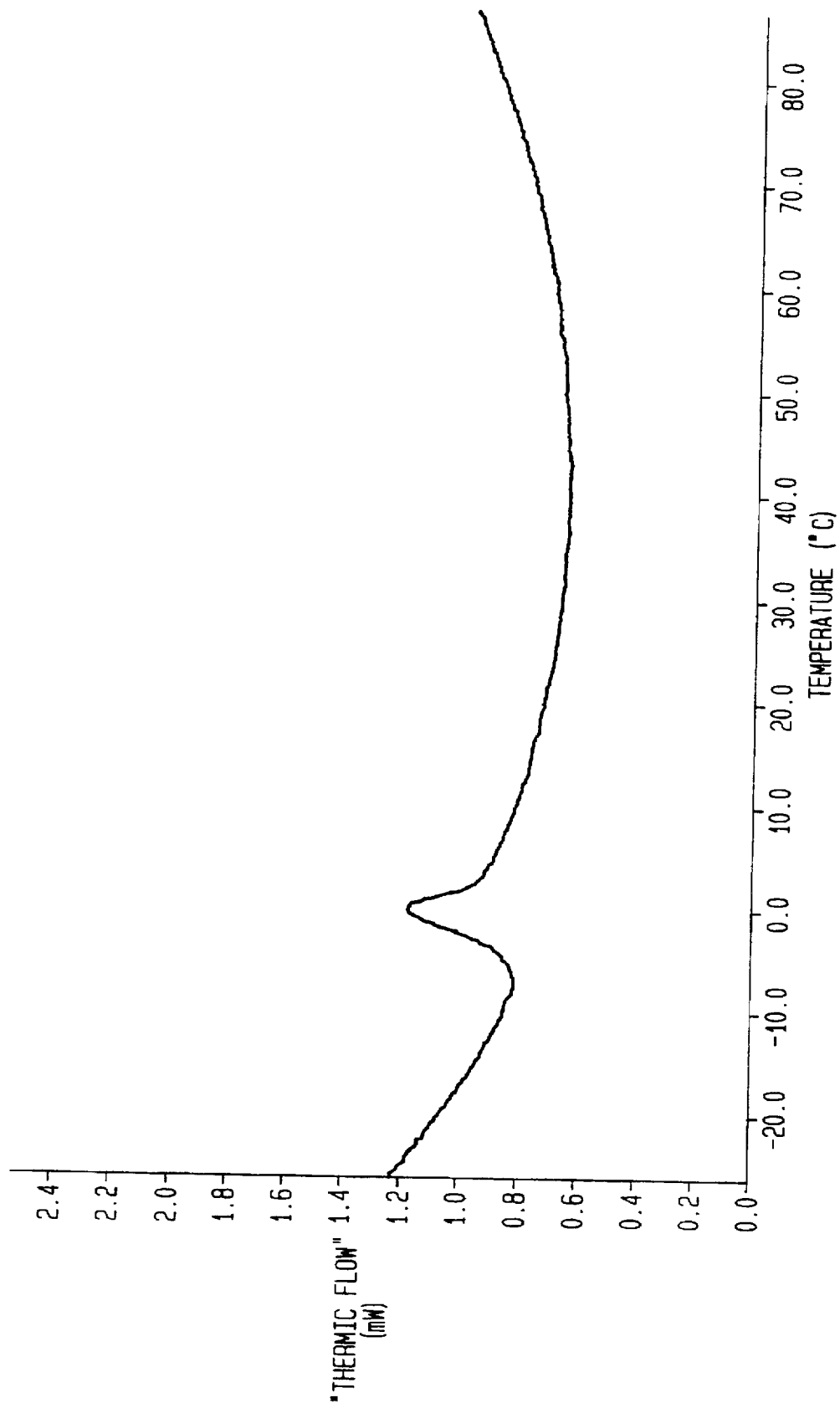
FIG. 5 is a differential thermal analysis curve showing the glass transition temperature of 2-(3-benzoylphenyl) propionic acid.

The glass transition temperature is at about −5° C., as revealed in FIG. 5 which is a differential thermal analysis curve obtained for a heating rate of 5° C./min (determined on a Perkin-Elmer® machine), which represents the variation in heat flow (expressed in mW) as a function of the temperature (expressed in °C.).

The running conditions are specified in Table III.

TABLE III

| | |
|---|---|
| Diameter of the nozzle hole | 400 µm |
| Frequency of vibration of the nozzle (2) | 435 Hz |
| Positive pressure of nitrogen (3) | 0.51 bar |
| Temperature of the molten product at (2) | 95° C. |
| Flow rate of the product at the nozzle outlet (2) | 0.840 kg/h |
| Tower inlet (5) air temperature | −35° C. |
| Tower outlet (6) air temperature | −20° C. |
| Fluid bed (11) air temperature | −35° C. |
| Fluid bed (13) air temperature | −10° C. |

After functioning for 60 minutes, 840 g of vitrified pearls are recovered in the fluid bed (13).

10 g of 2-(3-benzoylphenyl)propionic acid powder are added at (13).

The fluid bed (13) air temperature is increased.

The rate of temperature increase is 0.5° C./min.

The final fluidization temperature is 40° C.

After fluidization for 100 minutes, 840 g of crystallized pearls having a diameter of 940 µm are recovered. They are separated from the excess powder which served as crystallization seeds, by simple screening.

What is claim is:

1. A process for the preparation of crystallized pearls of a product exhibiting supercooling comprising the steps of:
    1) preparing a molten mass of the product,
    2) breaking up the molten mass into droplets,
    3) cooling the droplets to a temperature below the glass temperature of the product to form pearls, so that the droplets harden by vitrification,
    4) maintaining the pearls thus vitrified at a temperature below the glass transition temperature and thereafter placing said pearls in contact with crystallization seeds,
    5) crystallizing the pearls by raising the temperature above the glass transition temperature, and
    6) recovering the crystallization pearls in a recovery Art Unit: 1304 system.

2. A process according to claim 1 wherein at step 2) the molten mass is passing through a nozzle so as to form droplets, and at step 3) the droplets are solidifyied and are allowed to fall in a tower with a countercurrent of a cold gas, and then are recovered as vitrified pearls.

3. A process according to claim 1 wherein the product is selected from the group consisting of glyceryl guaiacolate, 2-(3-benzoylphenyl)propionic acid, 2-(4-isobutylphenyl) propionic acid and 2-methyl-2-propyl-1,3-propanediol dicarbonate.

4. A process according to claim 1 wherein the product at step 1) is melted at its melting point.

5. A process according to claim 1 wherein the product at step 1) is melted at a temperature not more than 5° C. above its melting point.

6. A process according to claim 3 wherein the product is glyceryl guaiacolate which is melted at step 1) at a temperature of between 83° C. and 88° C.

7. A process according to claim 1 wherein the step 2) the molten mass is transformed into droplets by passage through a nozzle.

8. A process according to claim 7 wherein the nozzle is a one-hole nozzle or a multi-hole nozzle with a number of holes ranging between 1 and 100.

9. A process according to claim 8 wherein the nozzle contains perforations whose diameter ranges between 50 and 2,000 µm and is preferably between 200 and 600 µm.

10. A process according to claim 7 wherein the nozzle used is a static nozzle.

11. A process according to claim 7 wherein the nozzle used is a nozzle subjected to a system of high frequency vibration.

12. A process according to claim 11 wherein the frequence is between 100 to 10,000 hertz.

13. A process according to claim 7 wherein at step 3) the droplets are further placed in contact with a cold fluid whose temperature is below the glass transition temperature of the product.

14. A process according to claim 13 wherein the cold fluid is a cold gas.

15. A process according to claim 13 wherein the cold gas is selected from the group consisting of nitrogen, air and oxygen-depleted air.

16. A process according to claim 13 wherein the temperature of the cold fluid is at a temperature 10° to 20° C. lower than the glass transition temperature of the product.

17. A process according to claim 13 wherein the temperature of the cold gas is between −60° C. and −30° C. and the product is glyceryl guaiacolate.

18. A process according to claim 17 wherein the temperature of the cold gas is between −60° C. and −40° C.

19. A process according to claim 14 wherein the cold gas is co-current with the droplets leaving the nozzle.

20. A process according to claim 19 wherein the cold gas is air or nitrogen.

21. A process according to claim 19 wherein the cold gas is between room temperature and 80° C.

22. A process according to claim 7 wherein the residence time of the droplets from leaving the nozzle of step 1) to its arrival in the recovery system of step 6) is between 1 and 10 seconds.

23. A process according to claim 22 wherein the residence time is between 1 and 3 seconds.

24. A process according to claim 1 wherein the recovery system of the vitrified pearls is a fluid bed technique.

25. A process according to one of claim 1 wherein at step 4) the vitrified pearls are maintained at a temperature of 5° to 10° C. below the glass transition temperature and at step 5) are placed in contact with crystallization seeds.

26. A process according to claim 25 wherein the temperature of the vitrified pearls is between −30° C. and −35° C. and the product is glyceryl guaiacolate.

27. A process according to claim 25 wherein the crystallization seeds consist of a small amount of crystalline powder of the same nature as the product.

28. A process according to claim 25 wherein the amount of seeds represents from 0.1 to 5% relative to the weight of the vitrified pearls.

29. A process according to claim 25 wherein at step 5) the temperature of the pearls is gradually raised to a temperature 10° to 20° C. above the glass transition temperature.

30. A process according to claim 29 wherein the temperature is gradually raised by 0.5° to 1° C. per minute.

31. A process according to claim 30 wherein at step 6) the recovery system of the crystallized pearls is a fluid bed technique.

* * * * *